US006787329B1

(12) United States Patent
Wei et al.

(10) Patent No.: US 6,787,329 B1
(45) Date of Patent: Sep. 7, 2004

(54) FLUOROGENIC PROTEASE SUBSTRATES BASED ON DYE-DIMERIZATION

(75) Inventors: Ai-Ping Wei, Woodbury, MN (US); Michael George Williams, Vadnais Heights, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/448,633

(22) Filed: Nov. 24, 1999

Related U.S. Application Data

(63) Continuation-in-part of application No. 08/846,828, filed on May 1, 1997, now abandoned.

(51) Int. Cl.[7] ............................. C12Q 1/37; C12Q 1/04; C07K 7/06
(52) U.S. Cl. ............................ 435/23; 435/29; 530/333
(58) Field of Search ............................ 435/29, 23, 7.2, 435/7.4, 40.52, 212; 530/330–333; 549/327

(56) References Cited

U.S. PATENT DOCUMENTS

| 4,314,936 A | | 2/1982 | Yaron et al. ............... 260/112.5 |
|---|---|---|---|
| 4,822,746 A | | 4/1989 | Walt ............................ 436/528 |
| 5,235,039 A | * | 8/1993 | Heath, Jr. et al. |
| 5,254,477 A | | 10/1993 | Walt ............................ 436/172 |
| 5,605,809 A | | 2/1997 | Komoriya et al. ............. 435/23 |
| 5,714,342 A | * | 2/1998 | Komoriya et al. |
| 5,723,307 A | | 3/1998 | Tsai et al. ....................... 435/24 |
| 5,741,657 A | * | 4/1998 | Tsien et al. |

FOREIGN PATENT DOCUMENTS

| EP | 0 428 000 A1 | 5/1991 | ............ C12Q/1/37 |
|---|---|---|---|
| GB | 2 278 356 A | 11/1994 | ............ C07K/15/00 |
| GB | 22-78356 | * 11/1994 | |
| WO | WO 95/03429 | 2/1995 | ............ C12Q/1/68 |
| WO | WO 96/13607 A | 5/1996 | ............ C12Q/1/37 |
| WO | WO 96/21040 | 7/1996 | |

OTHER PUBLICATIONS

Wel et al. Antibody–Mediated Fluorescence Enhancement Based on Shifting the Intramolecular Dimer=Mionomer Equilibrium of fluorescent Dyes Analytical Chemistry, vol. 66, No. 9, May 1, 1994.*

Manafi et al. Fluorogenic and Chromogenic Substrates Used in Bacterial Diagnostics Microbiological Reviews Sep. 1991 p. 335–348.*

Rohatgi et al. Nature of Bonding in Dye Aggregates vol. 70. No. 6 Jun. 1966.*

Livingston, D.C.; Brocklehurst, J.R.; Cannon, J.F.; Leytus, S.P.; Wehrly, J.A.; Peltz, S.W.; Peltz, G.A.; Mangel, W.F., "Synthesis and characterization of a new fluorogenic active–site titrant of serine protease"; Biochem, 1981, 20, pp. 4298–4306.

Lottenberg, R.; Christensen, U.; Jackson, C.M.; Coleman, P.L., "Assay of Coagulation Proteases Using Peptide Chromogenic and Fluorogenic Substrates"; Methods in Enzymology 1981, 80, pp. 341–361.

Manafi, M.; Kneifel, W.; Bascomb, S., "Fluorogenic and Chromogenic Substrates used in Bacterial Diagnostics"; Microbiological Reviews 1991, 55, pp. 335–348.

Rohatgi and G. S. Singhal, J. Phys. Chem., 1966, 70, pp. 1695–1701.

Stryer et al., "Energy Transfer: Spectroscopic Ruler"; Biochemistry, 1967, 58, pp. 719–726.

Packard, B.A.; Toptygin, D.D.; Komoriya, A.; and Brand, L.; "Profluorescent Protease Substrates: Intramolecular Dimers Described By The Exciton Model", Proc. Natl. Acad. Sci. USA, vol. 93, pp. 11640–11645, Oct. 1996.

Packard, B. Z., Toptygin, D.D., Komoriya, A., and Brand, L.; "Design Of Profluorescent Protease Substrates Guided By Exciton Theory", Methods in Enzymology, vol. 278, pp. 15–23, 1997.

Packard, B. Z., Toptygin, D. D., Komoriya, A., and Brand, L.; "Characterization Of Fluorescene Quenching In Bifluorophoric Protease Substrates", Biophysical Chemistry, vol. 67, pp. 167–176, 1997.

Packard, B. Z., Komoriya, A., Toptygin, D. D., and Brand, L.; "Structural Characteristics Of Fluorophores That Form Intramolecular H–Type Dimers In A Protease Substrate", J. Phys. Chem., vol. 101, No. 25, pp. 5070–5074, 1997.

Geoghegan, K. F., Rosner, P. J., Hoth, L. R., "Dye–Pair Reporter Systems For Protein Peptides Molecular Interactions", Bioconjugate Chem, vol. 11, No. 1, pp. 71–77, 2000.

* cited by examiner

Primary Examiner—Marjorie Moran
(74) Attorney, Agent, or Firm—Jean A. Lown; Melanie G. Gover

(57) ABSTRACT

A method of biological assay comprises the steps of providing an enzyme substrate comprising two fluorescence dye groups bound to a flexible peptide, the dye groups being of proximity sufficiently close so as to allow free energy attractions to draw the dyes together to essentially self-quench fluorescence of the dye groups, wherein self quenching of fluorescence of the dye groups is effected by dye dimerization or stacking, and enzymatically cleaving the peptide to release the fluorescence dye groups from dye dimerization or stacking, thereby producing an increase in fluorescence intensity. A protease substrate for use in the method of the invention is also disclosed. This invention finds use in detection and identification of microorganisms, sterilization assurance, pharmaceutical discovery, enzyme assays, immunoassays, and other biological assays.

17 Claims, 2 Drawing Sheets

FLUOROGENIC PROTEASE SUBSTRATES BASED ON DYE-DIMERIZATION

This application is a continuation-in-part application of U.S. application Ser. No. 08/846,828, filed on May 1, 1997 now abandoned.

FIELD OF THE INVENTION

This invention relates to a method of preparing and using protease substrates that become highly fluorescent upon enzymatic hydrolysis. This invention finds use in detection and identification of microorganisms, sterilization assurance, pharmaceutical discovery, enzyme assays, immunoassays, and other biological tests.

BACKGROUND OF THE INVENTION

Proteases are a class of enzymes that catalytically hydrolyze peptide bonds. Their primary chemical sequence and unique three-dimensional structure determine their activity and specificity. Depending on the active site composition, proteases are classified into major groups including aspartic, metallo-, thiol-, and serine proteases. The role of proteases in physiological processes is widely recognized. Not only are they involved in such functions as digestion, blood coagulation and fibrinolysis (Lottenberg, R.; Christensen, U.; Jackson, C. M.; Coleman, P. L., *Assay of Coagulation Proteases Using Peptide Chromogenic and Fluorogenic Substrates; Methods in Enzymology* 1981, 80, 341–361), but also in ovulation, tumorigenicity, immune response, and viral and bacterial infection, etc. (Livingston, D. C.; Brocklehurst, J. R.; Cannon, J. F.; Leytus, S. P.; Wehrly, J. A.; Peltz, S. W.; Peltz, G. A.; Mangel, W. F., *Synthesis and characterization of a new fluorogenic active-site titrant of serine protease; Biochem.* 1981, 20, 4298–4306). For example, retroviruses such as HIV are known to encode a protease which functions to process precursor proteins at specific cleavage sites. These cleavages occur during the virion assembly and are required for the maturation of infectious virus particles. Thus, inhibition of these proteases has become an important target for the design of antiviral agents, including those for AIDS.

In addition, public awareness of antibiotic resistant bacteria strains and food-borne illnesses is increasing. The management of microbial risks in healthcare, cosmetics, food and beverage industries is a serious health and safety issue. Bacterial testing is an integral part of managing microbial risks. The ability of many bacteria to produce proteases is a widely used criterion for identification and characterization of certain pathogenic species.

Sensitive and quantitative enzyme assays are required for the discovery and understanding of biological functions of proteases, the diagnosis of physiological disorders and the development of therapeutical drugs. A variety of techniques have been used to measure protease activities, including enzyme-linked immunosorbent assays (ELISA), high performance liquid chromatography (HPLC), protein immunoblot analysis, and thin layer electrophoretic analysis. However, these methods usually required multiple steps and multiple reagents, and are slow and expensive to operate. They are sometimes impractical for applications such as high-throughput screening of pharmaceutical drugs, e.g., protease inhibitors.

Fluorogenic substrates are molecules that change from nonfluorescent to highly fluorescent upon enzymatic hydrolysis. They are widely used as molecular probes for studies and tests of viral and bacterial proteases, nucleases, saccharidases, phosphatases and kinases (Manafi, M.; Kneifel, W.; Bascomb, S., *Fluorogenic and Chromogenic Substrates used in Bacterial Diagnostics; Microbiological Reviews* 1991, 55, 335–348). The fluorescence can be readily observed under UV illumination, by a fluorescent microscope, in a 96-well plate reader, or in a flow cytometer.

Several fluorogenic protease substrates are available commercially. Examples include EnzCheck™ kits (Molecular Probes, Inc., Eugene, Oreg.), which use highly-quenched casein substrates bearing 4,4-difluoro-4-borata-3a-azonia-4a-aza-s-indacene fluorophores sold under the trade name BODIPY (Molecular Probes, Eugene, Oreg.). When cleaved, fluorescent BODIPY-peptides are released. Typically, a two-fold increase in fluorescence intensity, at 530 nm, is observed for trypsin concentrations of up to 500 ng/mL. A fluorogenic substrate for HIV protease is available (Molecular Probes, Inc.) that includes the HIV protease cleavage site and, on one side thereof, the fluorophore 5-((2-aminoethyl)amino)naphthalene-1-sulfonic acid (EDANS) and on the other side thereof, the acceptor chromophore 4-(5-dimethylaminophenyl)azobenzene sulfonic acid (DABCYL). As described in European Patent Application No. 428,000, EDANS fluorescence is quenched by the DABCYL chromophore through intramolecular resonance energy transfer, a process requiring that the donor and acceptor be separated by no more than 100 Angstroms along the peptide chain. The fluorophore is excited by radiation at 340 nm and fluoresces at 490 nm, which can be obscured by absorbance or fluorescence of the bacterial culture medium.

U.S. Pat. No. 4,314,936 describes an enzyme assay substrate comprising an uninterrupted peptide chain to which is attached a fluorescent group in one part of the peptide and a fluorescence quenching group in another part. Cleavage of the chain at any point between the two liberates the fluorophore for detection and quantification. Specific amino acid sequences are prepared for specific enzymes. Fluorophores include eosinyl-, rhodaminyl-, and fluroesceinyl-type dyes as well as EDANS-type moieties. Quenching species (which are not dyes or fluorophores) include nitrosated aromatic compounds such as nitrophenyl, nitrobenzyloxycarbonyl, nitrobenzoyl, etc.

PCT Patent Application No. WO 95/03429 describes an immunoassay procedure wherein a fluorogenic tracer comprises a short antigen-mimicking peptide labeled with both a fluorescent energy transfer donor and a fluorescent energy acceptor. When free in solution, the tracer exhibits very little fluorescence due to intramolecular dye dimerization (quenching); when bound to an antibody of the native antigen, fluorescence is considerably increased due to dissociation of the molecular dimer brought about by conformational changes in the tracer peptide. Representative fluorescent energy dyes that form intramolecular dimers include the fluorescein family, such as fluorescein, tetramethyl rhodamine, rhodamine B, and Texas Red. Thus, the application describes fluorescence enhancement upon binding rather than fluorescence upon cleaving, and fluorescence quenching relies on a combination of energy transfer and dye dimerization.

U.S. Pat. Nos. 4,822,746 and 5,254,477 describe quantitative and qualitative analysis of analytes that relies upon the interaction of a fluorophore with a chromophoric light absorbing compound or with a second (light absorbing) fluorophore. Quenching occurs via both radiative and nonradiative energy transfer by the fluorophore when in the excited state, rather than by dye dimerization. By this means, the method of '746 is able to produce only a 10–20% increase in fluorescence in the presence of an analyte.

U.S. Pat. No. 5,605,809 describes peptides useful for protease detection, the peptides having a fluorophore conjugated to each end and folded such that the fluorophores exhibit quenching via intramolecular energy transfer. When cleaved by a target protease, the fluorophores are released from close proximity and the resulting signal is detected and quantified. FIGS. 2A and 2B of '809 show that, at most, an 9-fold increase in fluorescence is seen on cleavage of the substrate. A large number of peptides, ranging in size from 2 to about 8, preferably 2 to about 6 amino acids in length, is described. The fluorescent indicators absorb and emit light in the visible region (400–700 nm).

Fluorescence dye quenching commonly takes place by a number of mechanisms, including energy transfer and dye dimerization. In both cases, when a molecule comprising a fluorescent dye donor and an acceptor (wherein acceptor may or may not be a fluorescent dye in the case of energy transfer) linked by a chain X is excited by input of energy, typically by irradiation with a specific wavelength of light, energy is transferred from the donor dye to the acceptor rather than being dissipated by fluorescence. Energy Transfer, also referred to as Förster-type dipole-dipole interaction, generally takes place over a longer distance between donor and acceptor (on the order of 100 Angstroms). See, for example, L. Stryer et al., *Energy Transfer: Spectroscopic Ruler; Biochemistry*, 1967, 58, 719–726. Dye Dimerization or Dye Stacking, on the other hand, occurs when two or more fluorescence molecules are separated by a short-enough distance for their planar aromatic rings to interact to form aggregates such as dimers and trimers. The absorbance spectra of dyes in a dimer- or stacked state are substantially different from those of the same dye in energy transfer pairs. Dye dimer absorption spectra show characteristic decrease in the principal absorption peak as dye concentration increases, while showing a characteristic increase in the shoulder peak. This phenomenon is commonly referred to as "band splitting." See, for example, K. K. Rohatgi and G. S. Singhal, *J. Phys. Chem.*, 1966, 70, 1695–1701. See also, FIG. 2 (infra). Concentration increases can be accomplished either by increasing the amount of dye in a unit volume, or by physically locating two (or more) dye molecules closely together on a linker molecule, such as a peptide or other small molecule. Dimerization or stacking takes place through the formation of ground-state state complexes (i.e., through close physical contact), whereas energy transfer interactions occur through space. Because of this, these spectral changes are not seen for dyes that interact by energy transfer mechanisms.

SUMMARY OF THE INVENTION

Briefly, this invention provides a method of biological assay comprising the steps of:
  providing an enzyme substrate comprising two or more fluorescence dye groups bound to a flexible peptide comprising one or more enzymatically-cleavable bonds, the dye groups being of sufficiently close proximity to allow free energy attractions to draw the dye groups together so as to essentially self-quench fluorescence of the dye groups, wherein self-quenching of fluorescence of the dye groups is effected by dye dimerization or stacking, preferably dye dimerization, and
  enzymatically cleaving one or more of the enzymatically-cleavable bonds to release the fluorescence dye groups from dye dimerization or dye stacking, thereby resulting in increase in fluorescence intensity.

In a preferred embodiment, this invention provides a protease substrate comprising a peptide including two fluorescent dye groups, the dye groups being of proximity sufficiently close so as to essentially quench fluorescence of the dye groups by intramolecular dimer formation.

It is to be appreciated that more than two fluorescent groups can be bound to the peptide of the protease substrate and can participate in the intramolecular quenching.

A method of detecting a microorganism which produces a characteristic enzyme comprising the steps: a) providing an enzyme substrate specific for said characteristic enzyme comprising two or more fluorescence dye groups bound to a flexible peptide comprising one or more bonds cleavable by said characteristic enzyme, the dye groups being of proximity sufficiently close to allow free energy attractions to draw the dye groups together so as to essentially self-quench fluorescence of the dye groups, wherein self quenching of fluorescence of the dye groups is effected by dye dimerization or stacking, and b) cleaving one or more of said cleavable bonds of the peptide by said characteristic enzyme to release the fluorescence dye groups from dye dimerization, and producing an increase in fluorescence intensity.

Preferably, the substrate comprises a flexible short peptide with two molecules of a fluorescent dye (e.g., tetramethylrhodamine). The peptide provides affinity and specificity for the enzyme. Before hydrolysis, the dye molecules form an intramolecular dimer due to close proximity, which allows free energy attractions to draw the dye molecules together, resulting in significant fluorescence quenching. Enzymatic hydrolysis of a specific peptide bond produces a significant increase in fluorescence intensity because the dye groups dissociate from each other. The fluorescence can be readily observed under UV illumination, by a fluorescent microscope, in a 96-well plate reader, or in a flow cytometer. Preferably, fluorescent radiation is emitted in the visible spectrum. Fluorogenic substrates are homogeneous since no other developing reagents are required. This is important because it allows for detection and identification of microorganisms to be performed by using the primary isolation media, thus bypassing the need for time-consuming isolation procedures prior to identification.

In this application:
  "dye dimerization" means formation of a complex between two dye groups;
  "dye stacking" means formation of a complex between two or more dye groups;
  "fluorescence" means light emission by a substance at a given wavelength upon absorbing light of a different wavelength, wherein light emission occurs only during light absorption;
  "molar absorptivity" means the relative light absorption of a light absorbing species, calculated as the absorbance per molar concentration per 1 cm path length of light;
  "fluorescent quantum yield" means the ratio of the number of fluorescent photons emitted by an emitting substance to the total number of photons absorbed by the substance;
  "fluorophore" means a molecule that emits light at a given wavelength when stimulated by absorption of light of a different (usually shorter) wavelength.

This invention provides advantages over conventional methods for detection and identification of microorganisms. It provides a rapid and convenient homogeneous approach and employs chromogenic and fluorogenic substrates for measuring activities of extracellular and intracellular enzymes. The method and substrates of the invention have led to improved accuracy, faster detection and overall lower cost in detection and identification of microorganisms. In preferred embodiments, the present invention provides fluorogenic indicators that show a high signal level when cleaved and a very low noise level when intact, and that operate exclusively in the visible range. Additionally, this invention allows for examination of several bacteria simultaneously through judicious design and choice of peptides and the fluorophores attached thereto.

DETAILED DESCRIPTION OF PREFERRED EMBODIMENTS

Figure 1:
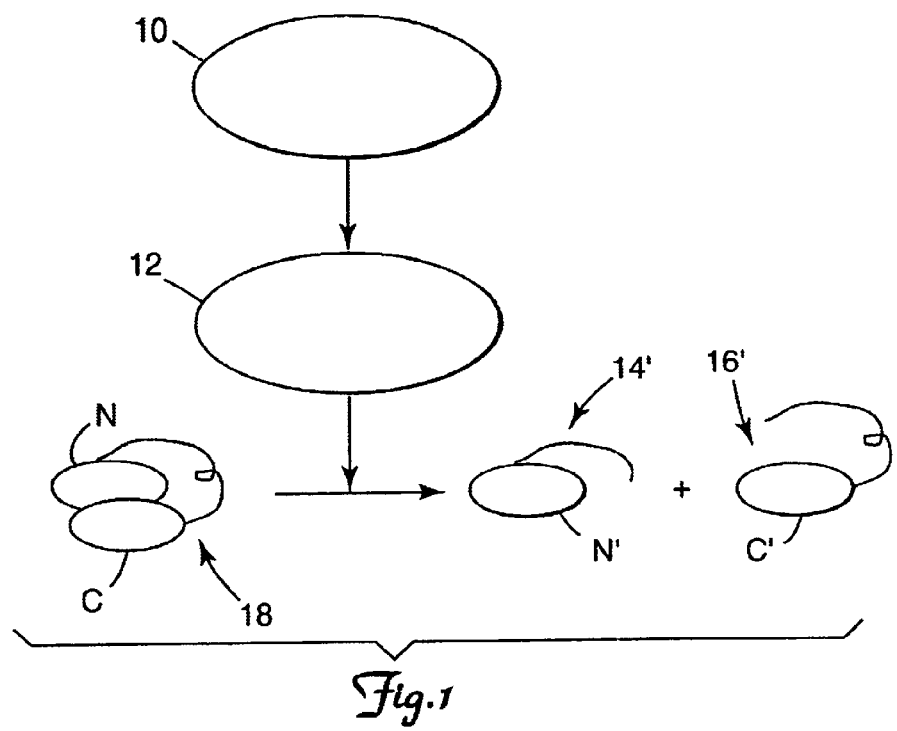
FIG. 1 is a conceptual illustration of a fluorogenic substrate based on dye-dimerization.

This invention provides a protease substrate and a method of biological assay using a flexible protease substrate comprising two or more fluorescent dye groups, the dye groups being in sufficiently close proximity to allow free energy attractions to draw the dye groups together so as to essentially quench fluorescence of the dye groups, the protease substrate having one or more enzymatically-cleavable bonds, wherein self-quenching of fluorescence is effected by dye stacking, preferably by dye dimerization, and enzymatically cleaving one or more of the enzymatically-cleavably bonds so that the resulting products each comprise a fluorescent dye group that produces an increase in fluorescence intensity.

The dye groups are fluorophores which preferably are separated from each other prior to cleavage by a distance of less than 100 Å.

Preferably, the method employs a substrate comprising two self-quenching fluorescence dye groups. More preferably, the method employs a substrate comprising two identical self-quenching fluorescence dye groups.

In another aspect the invention provides a fluorogenic enzyme substrate comprising at least two fluorescence dye groups covalently bound to a flexible peptide, the dye groups being in sufficiently close proximity to allow free energy attractions to draw the dye groups together to essentially self-quench fluorescence of the dye groups, wherein self-quenching of the dye groups is effected by dye dimerization or stacking. Preferably, at least two of the fluorescence dye groups are identical. More preferably, the fluorogenic enzyme substrate comprises two identical fluorescence dye groups.

Fluorescence is one of the most sensitive detection techniques available today. Zeptomolar amounts of enzyme molecules have been studied using a fluorescence microassay. Single enzyme molecules have been detected in an oil-dispersed droplet by fluorescence microscopy. Individual molecules of an enzyme have been manipulated electrophoretically in a capillary tube and monitored by fluorescence spectroscopy. See Xue, Q.; Yeung, E. S. *Differences in Chemical reactivity of Individuals molecules of an enzyme; Nature* 1995, 373, 681–683. Assays for detection of coliform bacteria using β-galactosidase as a marker enzyme have been developed. Fluorometry was found to have a 250-fold increase in sensitivity and 5 hour reduction in the time of detection, relative to colorimetric methods. See Van Poucke, S. O.; Neils, H. J. *Development of a Sensitive Chemiluminometric Assays for the Detection of β-Galactosidase in Permeabilized Coliform Bacteria and Comparison with Fluorometry and Colorimetry; Appl. Env. Microbiol.* 1995, 61, 4505–4509.

To prepare fluorogenic substrates of the invention, a selected relatively small peptide comprising 2 to 10 amino acids which are joined through peptide bonds is obtained as disclosed below and is then labeled with a pair of fluorescent dyes which, when appropriately bonded to the peptide to form a "conjugate", has the characteristic of dimerizing or "stacking" so as to quench any fluorescence of both fluorophores. The dyes in the pairs or multiple dye groups quench each other so that each dye acts as a fluorescence energy transfer donor and acceptor. The type of dyes which exhibit such dimerization or stacking characteristics when bonded to the small peptide within a sufficiently close proximity to one another include those dyes which have a generally planar aromatic structure so as to be capable of forming homo- or heterodimers when in solution at concentrations which are sufficiently high (for example, $10^{-2}$ to $10^{-4}$ M).

Dimerization or stacking of the fluorophores of the present invention is based on non-physical, free energy attraction forces between the dye molecules. Free energy forces include enthalpic energies such as h-bond, electrostatic, and hydrophobic forces. These forces are explained, for example, in Rohgati, K. K., Singhal, G. S., *Nature of Bonding in Dye Aggregates, The Journal of Physical Chemistry*, vol. 70, number 6, June 1966, pp. 1695–1701.

In order to allow free energy forces to pull the fluorophores together, the peptide substrates of the present invention must be flexible. A flexible peptide is one that has a configuration, structure, or amino acid composition that allows sufficient freedom of movement by the peptide structure such that free energy attractive forces between or among the dye molecules attached to the peptide dominate any physical constraints introduced into the substrate by the type, amount, or order of amino acids in the peptide to the extent that the attractive forces induce dimerization or stacking of the dye molecules. The substrates of the present invention preferably are flexible enough to assume numerous conformations and physical orientations. The structures should allow free rotation about single bonds capable of free rotation (at room temperature) and should allow the substrate to change configurations. In other words, the substrate has no conformation-determining regions such as those described in U.S. Pat. Nos. 5,605,809 and 5,714,342, which regions cause the substrate to have a rigid and/or fixed, structure.

The substrates may be comprised of a suitable number and type of amino acids such that it can achieve the necessary flexibility. Suitable amino acids may include, for example, glycine, alanine, arginine, asparagine, asparaginic acid, cystein, glutamine, glutaminic acid, histidine, isoleucine, leucine, lysine, methionine, phenylalanine, serine, threonine, tryptophan, tyrosine, and valine.

To maintain the requisite flexibility, the substrates of the present invention should have no or few amino acids that will limit the substrate structure to a specific configuration. Even if the substrate includes one or more amino acid that could introduce rigidity or a fixed configuration, the entire substrate should be flexible enough to allow the dye molecules to be brought together by free energy attractive forces.

The substrate may also have bend-introducing amino acids, such as proline, so long as the number and placement of the bend-introducing amino acids does not result in an overall fixed or rigid conformation.

The ability to use a flexible peptide structure in a fluorogenic substrate wherein fluorophore dimerization is achieved by free energy forces has not previously been appreciated in the art. For example, U.S. Pat. Nos. 5,605,809 and 5,714,342 require two conformation determining regions in a substrate to rigidly hold fluorophores together. U.S. Pat. Nos. 5,605,809 and 5,714,342 teach away from the usefulness of flexible substrates.

More particularly, fluorogenic protease substrates useful in the present invention can be made by chemical reaction of a flexible peptide of short length, preferably less than 100 Å, and two molecules of a fluorescent dye. Protease substrates are commercially available (e.g., GeneMed Biotechnologies, San Francisco, Calif.). Covalently bonding fluorescent dyes to protease substrates is well known in the art.

Representative peptides useful to produce the fluorogenic protease substrates include those flexible peptides having about 2 to 10 amino acids, preferably 4 to 8 amino acids, such that the dye groups can dimerize or stack and such that the peptide has an enzyme specific cleavable site. Upon cleavage of the substrate, however, the fluorescence intensity will be enhanced as a result of dissociation of the intramolecular dimers or stacks.

More preferably, substrates useful in the invention include at least one ARG-GLY sequence. Most preferably, the substrate comprises a peptide of the SEQ ID NO. 1 Val-Pro-Arg-Gly-Lys having fluorescent dye groups covalently attached at each terminal residue.

Fluorogenic protease substrates useful in the present invention can be made by methods known in the art; see for example, European Patent Application No. EP 0 428,000.

Useful fluorescent dyes for reacting the peptides to produce the protease substrates include those that undergo dye stacking. It is well known that some fluorescent dyes (e.g., fluoresceins, rhodamines, cyanines, boron-heterocyclic dyes such as 4,4-difluoro-4-borata-3a-azonia-4a-aza-s-indacene (BODIPY), etc.) form dimers in aqueous solution when they are within close proximity of each other.

Planar aromatic dyes of the fluorescein family, such as fluorescein, tetramethylrhodamine (TMR), rhodamine B, and a rhodamine dye sold under the trade name TEXAS RED Molecular Probes, Eugene, Oreg.) are representative dyes of this type. Due to the interaction between the transition dipoles of the resonating dimeric structure, the fluorescent quantum yield of the dimer will be quite low when no enzyme that can cleave the peptide is present. When the dimer dissociates after cleavage by the enzyme significantly higher fluorescence quantum yield in aqueous solution will be observed. In this manner, a homogenous enzyme assay can be designed wherein labeled peptide is placed in solution and the enzyme analyte is added, so that the enzyme cleaves the peptide, causing dimerization to decrease with an attendant increase in fluorescence.

Enzymatic cleavage is achieved by contacting the fluorogenic substrate with the specific enzyme or enzyme contacting medium.

Enzymes suitable for use in the present invention include all enzymes generally classified as proteases, ie., proteins that catalytically hydrolyze peptide bonds, including, for example, aspartic, metallo-, thiol, serine, retroviral, and trypsin proteases. Preferred enzymes include members of the trypsin family, such as thrombin, trypsin-like enzymes, etc.

Although there are many different types of fluorogenic substrates, the mechanisms by which they work may be classified into three major categories: chemical, physical, and physio-chemical.

The biological assay method of the present invention is homogeneous. It does not require separation steps as found in assay formats such as ELISA and bioluminescence. This translates to more efficient use of in reagents, labor, time and equipment for end-users and vendors alike. Typically, fluorophores used in the method of the invention absorb light in the ultraviolet range. Although useful, UV detection sensitivity can be reduced in biological samples containing molecules that absorb strongly in the ultraviolet. In addition, some noncleaved indicators have substantial background fluorescence. It is desirable to have fluorogenic indicators that show a high signal level when cleaved and a very low noise level when intact, and that operate exclusively in the visible range. The present invention teaches a method to provide these benefits and also offers the potential of examining several bacteria simultaneously through the judicious design and choice of peptides and the fluorophores attached thereto.

Dyes of the rhodamine family such as fluorescein, tetramethylrhodamine, X-Rhodamine, and Rhodamine B have very high fluorescent quantum yields (approximately 0.85) in the visible wavelength range (400–700 nm). For this reason they are frequently used as laser dyes, indicators, biological labels, for remote sensing, and for detection of minute amount of substances. Importantly, these dyes are known to form stacked dimers that self quench fluorescence when brought into close proximity such as at high concentrations ($\sim 10^{-2}$ to $10^{-4}$ M). For many applications this phenomenon is obviously undesirable. However, this phenomenon may also be used to advantage. If two dye molecules are attached, i.e., labeled, at each terminal residue of a short flexible peptide (2 to 10 amino acid residues), the labeled conjugate shows little fluorescence, due to self quenching. Because this is an effective increase in the local concentration, the conjugate will stay quenched regardless of the total concentration. When cleaved by an enzyme, the two labels are separated, producing high intrinsic fluorescence. Therefore, enzyme activity can be directly related to the net increase in fluorescence intensity. If the enzyme is secreted from eukaryotic or prokaryotic cells, the fluorescence intensity may be related to the metabolic activity of the cells. The ability of one enzyme molecule to turn over millions of substrate molecules is an amplification process. This amplification is further enhanced when the enzyme is from a live cell culture because more enzyme molecules are generated as the cells grow. This "double amplification", when coupled with fluorescence techniques, offers a promising approach to rapid, sensitive and specific detection of bacteria. This concept is illustrated in FIG. 1. 10 represents a bacterium, for example, *Staphylococcus aureus* or *Vibrio parahaemolyticus*, which produces an enzyme 12, for example, a or trypsin-like enzyme. 12 catalytically cleaves peptide substrate 18 (nonfluorescent) comprising two quenched fluorescent dye groups N and C to produce two product fragments 14' and 16' which comprise highly fluorescent dye groups N' and C'.

As noted above, representative peptides useful to produce fluorogenic protease substrates includes those peptides having about 2 to 10 amino acids such that the dye groups can stack and such that the peptide has an enzyme-specific cleavable site. Since there is a large number of proteases, there is an equally large number of peptides that can be useful in the invention. The specific requirement is that a target peptide must be flexible enough to allow free enrgy forces to draw the dye molecules together and must have the requisite chemical bond attacked by the protease. For example, as discussed below, trypsin is known to hydrolyze peptides on the carboxyl side of an arginine or lysine residue, so any peptide with this characteristic can be a trypsin substrate.

*Vibrio parahaemolyticus* is a pathogen that causes seafood-related poisoning and produces a trypsin-like enzyme intracellularly that is commonly used as a marker for identification of *Vibrio parahaemolyticus*. It specifically hydrolyzes the peptide bond after the amino acid arginine. The enzyme is made available to contact with the fluorogenic substrate by the use of agents that increase the permeability of the outer membrane (OM). Ethylenediaminetetraacetic acid (EDTA) is commonly used for this purpose by effecting the outer membrane barrier of gram-negative enteric bacteria. It removes, by chelation, stabilizing divalent cations from their binding sites in lipopolysaccharides (LPS). This results in the release of a significant proportion of LPS from the cells. The loss of LPS will lead to the appearance of phospholipids in the outer leaflet of the OM, which would then act as channels through which hydrophobic compounds can diffuse. Under certain conditions, the OM becomes ruptured and permeable to macromolecules. See Vaara, M. *Agents that increase the permeability of the outer membrane; Microbiol. Reviews* 1992, 56 395–411.

Trypsin is a potent enzyme that cleaves any peptide bond after a positively charged Arg residue, independent of its neighboring residues. Other enzymes in the same family (e.g., thrombin), however, depend on the surrounding residues, a property that renders them their specificity.

Trypsin and trypsin-like enzymes are used as a model in FIG. 1 to demonstrate this concept. Trypsin is a highly specific proteolytic enzyme from the intestine and is among the most potent enzymes known. It hydrolyzes peptide bonds on the carboxyl side of an arginine or lysine residue. This property of trypsin is well characterized. To evaluate the inventive concept, the following sequence was designed:

(N-terminus) Val-Pro-ARG-GLY-Lys (C-terminus)  SEQ ID NO. 1 wherein the free amine is on the valine (N-terminus) and the free carboxylic acid is on lysine (C-terminus).

The amide bond between two residues (in bold) is the trypsin cleavage site. The role of flanking residues is to reduce steric hindrance when dyes are attached. The amino groups on Val and Lys are used to react with dye groups. The carboxyl group in the C-terminus can be used to attach to a solid support when appropriate.

The present invention differentiates itself from commercially available approaches using protease substrates in both the working mechanism and sensitivity. It has been found that the present invention provides at least 10-, 20-, 30-fold and higher increases in fluorescence compared to conventional assay kits available commercially which only result in a 2-fold increase in fluorescence using a protease substrate.

For rapid and sensitive tests, it is important to maximize the signal-to-noise ratio. Most traditional fluorogenic substrates emit in the far UV wavelength region (350–450 nm) where most bacteria growth media have significant auto fluorescence. For example, the culture medium for *Staphylococcus aureus* has two significant emission maxima at 425 nm and 475 nm when excited at 360 nm. In order to avoid this problem, high substrate concentrations are normally used. This can result in higher assay cost, higher toxicity to organism, and sometimes precipitation of substrate. The present invention overcomes the difficulty of autofluorescence interference by red-shifting the detection wavelength to the visible spectrum (tetramethylrhodamine: $\lambda_{ab}$=550 nm, $\lambda_{em}$=580 nm). Moreover, the concept described in this invention can be applicable to other dyes that will also red-shift the emission to even longer wavelengths. Typically, useful dyes can have the following characteristics: high extinction coefficient (>80,000 $cm^{-1}M^{-1}$); high quantum yields (>0.85 in aqueous solution); spectra that are insensitive to solvent and pH; good aqueous solubility, photostability; and high dimerization constant.

This invention finds use in, but is not limited to, detection and identification of microorganisms, sterilization assurance, pharmaceutical discovery, enzyme assays, and immunoassays. In addition, a fluorogenic substrate for HIV protease activity can be useful as a test for antiviral agents that may be useful in AIDS therapy.

Objects and advantages of this invention are further illustrated by the following examples, but the particular materials and amounts thereof recited in these examples, as well as other conditions and details, should not be construed to unduly limit this invention.

EXAMPLES

In the following examples,

Val or V=valine;

Pro or P=proline;

Arg or R=arginine;

Gly or G=glycine;

Lys or K=lysine;

TMR=tetramethylrhodamine or tetramethylrhodamine moiety;

Example 1

Preparation of Fluorogenic Protease Substrates

SEQ ID NO. 1 Val-Pro-Arg-Gly-Lys was synthesized by GeneMed Biotechnologies (South San Francisco, Calif.) and purified on reverse phase high performance liquid chromatography (HPLC). Its chemical identity was confirmed by Fast Atom Bombardment (FAB) mass spectroscopy and amino acid analysis. The peptide was reacted overnight with tetramethylrhodamine succimidyl ester in 0.1 M sodium bicarbonate, pH 8.3. The reaction mixture was purified on reversed phase HPLC (C-18 column, particle size 15 $\mu$m, Waters Corp., Milford, Mass.). All chemically reactive dyes were purchased from Molecular Probes, Eugene, Oreg. The dye-peptide conjugate had the chemical structure of SEQ ID NO. 2 TMR-Val-Pro-Arg-Gly-Lys-TMR (designated T-VPRGK-T in FIG. 2) as shown in Formula I, below. A composite gradient of acetonitrile (ACN) in water was used to purify this conjugate. In a typical elution, the acetonitrile content was increased from 15% to 30% during the initial 15 minutes, followed by a 10-minute isocratic elution at 30% ACN, a 5-minute gradient to 50%, then 5-minute isocratic elution at 50% ACN. All solvents contained 0.1% trifluoroacetic acid. The molecular weight of the purified conjugate, determined by FAB mass spectroscopy, was 1379 which was the calculated molecular mass based on the elemental composition of $C_{74}H_{85}N_{13}O_{14}$. This dual-labeled conjugate shown below, exhibited substantially lower fluorescence than its singly labeled counterpart.

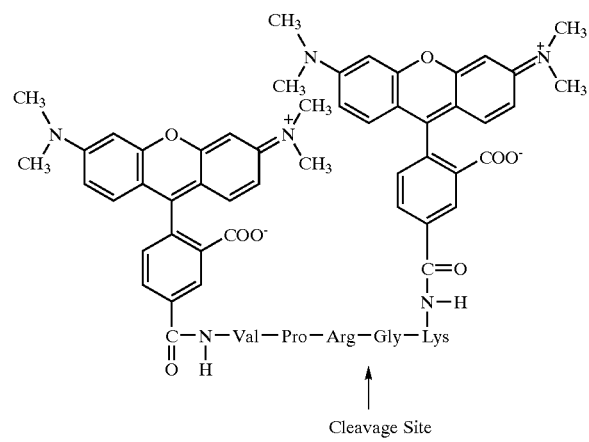

Cleavage Site

Example 2
Hydrolysis of Fluorogenic Protease Substrates by Purified Enzymes

Figure 2:
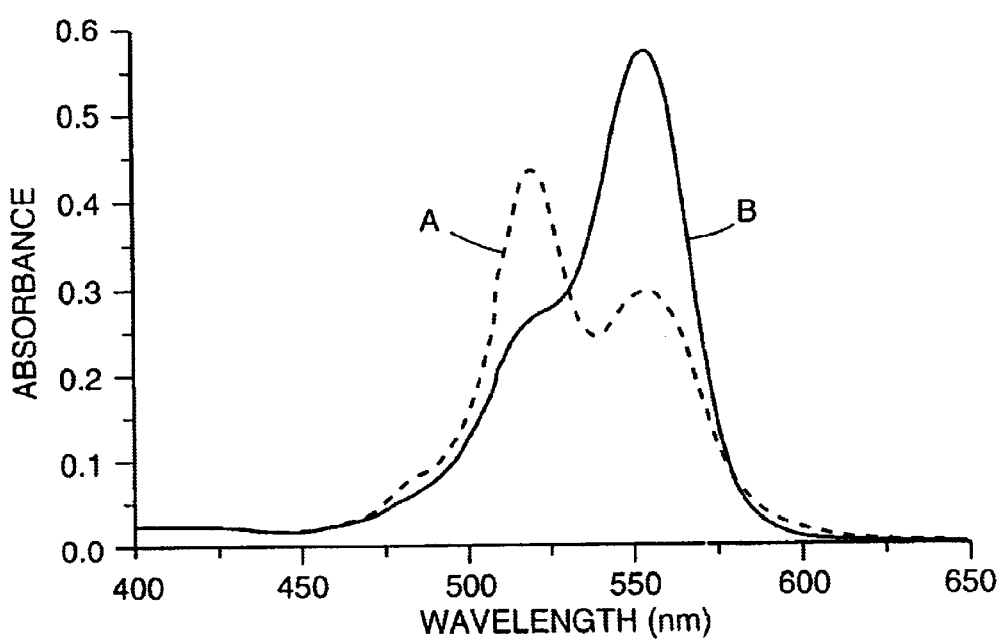
FIG. 2 shows the absorption spectra of T-VPRGK-T (approximately $10^{-5}$M) before (tracing A) and after (tracing B) enzymatic hydrolysis by trypsin (approximately $10^{-7}$M).

Enzymatic hydrolysis of the substrate from Example 1 was carried out in 50 mM carbonate buffer, pH 8.9 at room temperature. Fluorescence intensity of the solution prior to treatment with trypsin and after treatment with trypsin is shown in Table 1, for excitation wavelengths of 360 nm, 522 nm, 530 nm, and 553 nm, respectively. Besides increase in fluorescence intensity, changes in absorption spectra were also observed, as shown in FIG. 2. When intact, the conjugate had an absorption maxima at 520 nm with a shoulder at 550 nm (tracing A). This is a characteristic of dye dimerization or stacking, as described above. Cleavage resulted in reversal of the relative absorbance of the two peaks, reverting to the spectra of free tetramethyl rhodamine in aqueous solution (tracing B). Both the fluorescence and absorption results provided convincing evidence that ground-state interactions existed between dye molecules in the conjugate and became diminished after enzymatic cleavage.

The data of Table 1 show that, for a wide spectrum of excitation frequencies, fluorescence intensity of the cleaved substrate solution is as much as 29 times that of the intact substrate solution, averaging from 25 to 28 times the intensity, for emission wavelengths from 570 to 585 nm, a range easily visible to the human eye.

Example 3

Use of Fluorogenic Protease Substrates to Detect *Vibrio Paraeamolyticus*

Figure 3:
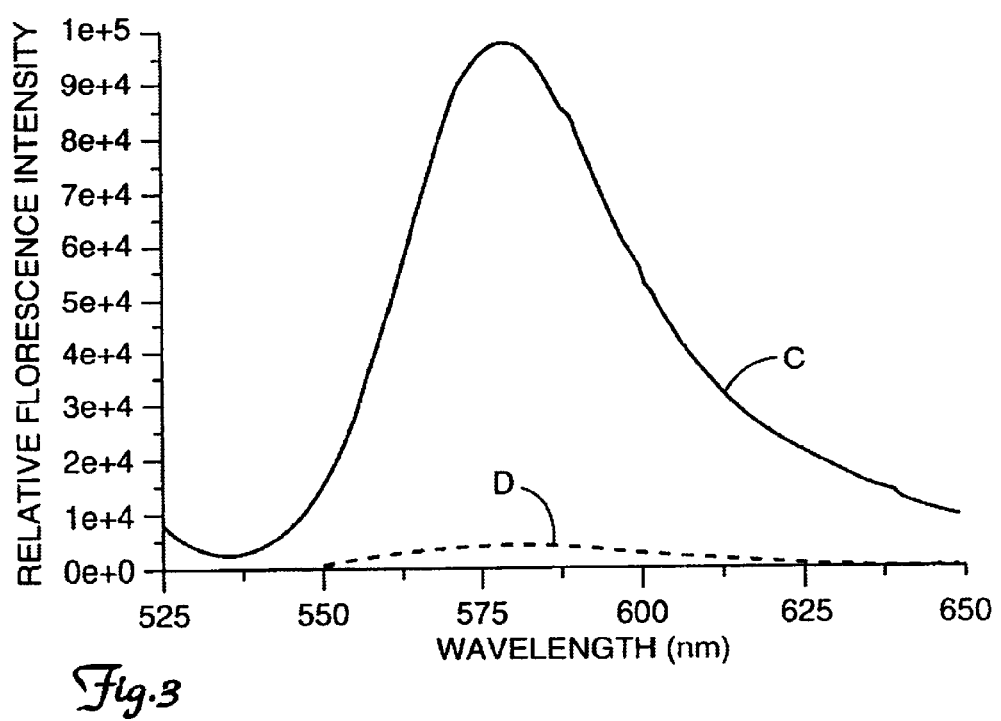
FIG. 3 shows fluorescence spectra before exposure (tracing D) and after exposure (tracing C) to a lysate of *Vibrio parahaemolyticus*.

*Vibrio parahaemolyticus* used in these experiments was a quality control strain for the Transport Swab System of Becton Dickinson Microbiology Systems (Cockeysville, Md.). It was purchased from American Tissue Culture Collection (ATCC accession no. 49398). Cells were grown at 37° C. in nutrient broth with 3 percent sodium chloride. Ten ml of overnight culture was centrifuged. Broth was disposed and 3 ml of assay buffer added (1 mM EDTA, 50 mM phosphate buffer at pH 7.2) containing 50 µl of dual labeled conjugate of formula I, 1000 dilution (see Example 1, procedure for making labeled peptide). To ensure complete cleavage the reaction mixture was incubated overnight. Fluorescence intensity of cuvettes with and without cells was measured, (tracings C and D, respectively). The resulting spectra are shown in FIG. 3.

Cleavage by the trypsin-like enzyme produced an increase in fluorescence. This assay provided a clear, rapid method that was not only detectable by a simple fluorometer, but also to the human eye only seconds after trypsin introduction.

Various modifications and alterations of this invention will become apparent to those skilled in the art without departing from the scope and spirit of this invention, and it should be understood that this invention is not to be unduly limited to the illustrative embodiments set forth herein.

TABLE 1

| Emission Wavelength (nm) | Excitation 360 nm | | | Excitation 522 nm | | | Excitation 530 nm | | | Excitation 553 nm | | |
|---|---|---|---|---|---|---|---|---|---|---|---|---|
| | w/o trypsin | w/ trypsin | ratio | w/o trypsin | w/ trypsin | ratio | w/o trypsin | w/ trypsin | ratio | w/o trypsin | w/ trypsin | ratio |
| 570 | 319 | 8625 | 27 | 1378 | 40193 | 29 | 1687 | 46615 | 28 | 3301 | 82385 | 25 |
| 571 | 347 | 8817 | 25 | 1525 | 41416 | 27 | 1718 | 48314 | 28 | 3402 | 85120 | 25 |
| 572 | 369 | 9322 | 25 | 1480 | 42506 | 29 | 1819 | 49955 | 27 | 3457 | 87845 | 25 |
| 573 | 365 | 9189 | 25 | 1509 | 43406 | 29 | 1844 | 50871 | 28 | 3658 | 89719 | 25 |
| 574 | 354 | 9629 | 27 | 1645 | 44241 | 27 | 1904 | 52163 | 27 | 3649 | 91555 | 25 |
| 575 | 410 | 9719 | 24 | 1643 | 45037 | 27 | 1895 | 52681 | 28 | 3802 | 93001 | 24 |
| 576 | 401 | 9759 | 24 | 1587 | 45519 | 29 | 1968 | 52855 | 27 | 3827 | 94046 | 25 |
| 577 | 378 | 9776 | 26 | 1672 | 45648 | 27 | 1939 | 53752 | 28 | 3816 | 94816 | 25 |
| 578 | 379 | 9981 | 26 | 1629 | 45980 | 28 | 1970 | 53611 | 27 | 3806 | 94516 | 25 |
| 579 | 392 | 9872 | 25 | 1673 | 45745 | 27 | 2026 | 53534 | 26 | 3962 | 94662 | 24 |
| 580 | 361 | 9788 | 27 | 1595 | 45757 | 29 | 1973 | 53414 | 27 | 3695 | 93715 | 25 |
| 581 | 375 | 9960 | 27 | 1665 | 44936 | 27 | 1985 | 53190 | 27 | 3825 | 93189 | 24 |
| 582 | 376 | 9783 | 26 | 1567 | 44724 | 29 | 1948 | 52569 | 27 | 3736 | 92281 | 25 |
| 583 | 347 | 9591 | 28 | 1599 | 44076 | 28 | 1926 | 51719 | 27 | 3724 | 91125 | 24 |
| 584 | 385 | 9387 | 24 | 1601 | 43282 | 27 | 1905 | 50705 | 27 | 3593 | 89415 | 25 |
| 585 | 353 | 9427 | 27 | 1527 | 42928 | 28 | 1820 | 49629 | 27 | 3449 | 87910 | 25 |
| Average | | | 26 | | | 28 | | | 27 | | | 25 |

We claim:

1. A method of biological assay comprising:
   a) providing an enzyme substrate comprising two or more identical fluorescence dye groups bound to a flexible peptide comprising one or more enzymatically cleavable bonds, the dye groups being drawn together by free energy attractions such that the dye groups together self-quench their fluorescence by dye stacking or dimerization, and
   b) contacting said substrate with a substance being assayed to determine the presence of an enzyme capable of cleaving an enzymatically cleavable bond wherein the enzymatic cleaving of said cleavable bond of the peptide will release the fluorescent dye groups from dye stacking or dimerizing, thereby producing a 24- to 29-fold increase in fluorscene intensity over that of the quenched dye groups thereby indicating the presence of said enzyme, wherein the emission wavelength of the fluorescent dye groups is at or above 570 nm.

2. The method according to claim 1 wherein said dye groups are separated from each other by a distance of less than 100 Å.

3. The method according to claim 1 wherein said released fluorescence dye groups emit radiation in the visible range.

4. The method according to claim 1 wherein said fluorescence dye groups have a planar configuration.

5. The method according to claim 1 wherein said dye groups are selected from the group consisting of fluorescein, rhodamine, and cyanine dye groups.

6. The method according to claim 1 wherein said dye groups are selected from the group consisting of fluorescein, tetramethylrhodamine, X-Rhodamine, Rhodamine B, and TEXAS RED.

7. The method according to claim 1 wherein said flexible peptide comprises from 2 to about 10 amino acids, wherein said dye groups bound to said peptide form a dye dimer or stack and wherein said peptide has at least one enzyme cleavable bond.

8. The method according to claim 1 wherein said enzyme involved in said enzymatic cleaving is selected from the group consisting of aspartic, metallo-, thiol, serine, retroviral, and trypsin proteases.

9. A protease substrate comprising a flexible peptide and including two identical fluoresence dye groups that are drawn together by free energy attractions so as to self-quench fluorescence of the dye groups by intramolecular dimerization or stacking and which, when separated, fluoresce at a 24- to 29-fold increase in fluorescence intensity over that of the quenched dye groups, wherein the emission wavelength of the fluorescent dye groups is at or above 570 nm.

10. The protease substrate according to claim 9 wherein said dye groups of an intramolecular dimer formed by said intramolecular dimerization are separated by a distance of less than 100 Å.

11. The protease substrate according to claim 9 wherein said dye groups comprise a fluorescense donor and acceptor.

12. The protease substrate according to claim 9 wherein said dye groups have a planar configuration.

13. The protease substrate according to claim 9 wherein said dye groups are selected from the groups consisting of fluorescein, rhodamine, and cyanine dye groups.

14. The protease substrate according to claim 9 wherein said dye groups are selected from the groups consisting of fluorescein, tetramethylrhodamine, X-Rhodamine, Rhodamine B, and TEXAS RED.

15. The protease substrate according to claim 9 wherein said peptide comprises from 2 to about 10 amino acids, wherein said dye groups bound to said peptide form a stack, and wherein said peptide has at least one enzyme-specific cleavable bond.

16. The protease substrate according to claim 9 having the formula of SEQ ID NO. 2:
    TMR-Val-Pro-Arg-Gly-Lys-TMR.

17. An assay method of detecting a microorganism, which microorganism produces a characteristic enzyme, comprising:
    a) providing an enzyme substrate specific for said characteristic enzyme produced by said microorganism comprising two or more identical fluorescence dye groups bound to a flexible peptide comprising one or more bonds cleavable by said characteristic enzyme, the dye groups being drawn together by free energy attractions such that the dye groups self-quench their fluorescence by dye dimerization or stacking, and
    b) cleaving one or more of said cleavable bonds of the peptide by said characteristic enzyme to release the fluorescence dye groups from dye dimerization or stacking, thereby producing a 24- to 29-fold increase in fluorescence intensity over that of the quenched dye groups thereby indicating the presence of said microorganism, wherein the emission wavelength of the fluorescent dye groups is at or above 570 nm.

* * * * *

UNITED STATES PATENT AND TRADEMARK OFFICE
CERTIFICATE OF CORRECTION

PATENT NO. : 6,787,329 B1
DATED : September 7, 2004
INVENTOR(S) : Wei, Ai-Ping

It is certified that error appears in the above-identified patent and that said Letters Patent is hereby corrected as shown below:

Column 2,
Line 21, delete "Fluorescene" and insert in place thereof -- Fluorescence --.

Column 3,
Line 45, delete "state".

Column 7,
Line 46, insert -- ( -- before "Molecular".

Column 9,
Line 29, insert -- , -- after "56".

Column 15,
Line 35, delete "fluorscene" and insert in place thereof -- fluorescence --.
Line 64, delete "fluoresence" and insert in place thereof -- fluorescence --.

Column 16,
Line 29, delete "fluorescence" and insert in place thereof -- fluorescence --.

Signed and Sealed this

Eighth Day of February, 2005

JON W. DUDAS
*Director of the United States Patent and Trademark Office*

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
         (A) LENGTH: 5
         (B) TYPE: amino acid
         (C) STRANDEDNESS: single
         (D) TOPOLOGY: linear (ii) MOLECULE TYPE: <Unknown>
         (A) DESCRIPTION: peptide (iii) HYPOTHETICAL: no (iv) ANTI-SENSE: no (v) FRAGMENT TYPE:
         (A) N-terminal
         (B) C-terminal (vii) IMMEDIATE SOURCE:
         (A) LIBRARY: Manufacturer (GeneMed Biotechnologies, South San
             Francisco, CA, USA)

(ix) FEATURE:
         (A) NAME/KEY:  peptide
         (B) LOCATION:  1 . . 5
         (C) IDENTIFICATION METHOD:   Synthesis; verified by FAB mass
             spectroscopy and amino acid analysis (xi) SEQUENCE DESCRIPTION: SEQ ID NO: 1:

Val Pro Arg Gly Lys
1               5

(2) INFORMATION FOR SEQ ID NO: 2:

(i) SEQUENCE CHARACTERISTICS:
         (A) LENGTH: 5
         (B) TYPE: amino acid
         (C) STRANDEDNESS: single
         (D) TOPOLOGY: linear (ii) MOLECULE TYPE: <Unknown>
         (A) DESCRIPTION: peptide (iii) HYPOTHETICAL: no (iv) ANTI-SENSE: no (v) FRAGMENT TYPE:
         (A) modified C-terminal
         (B) modified N-terminal (vii) IMMEDIATE SOURCE:
         (A) LIBRARY: Manufacturer (GeneMed Biotechnologies, South San
             Francisco, CA, USA)

(ix) FEATURE:
         (A) NAME/KEY:  peptide
         (B) LOCATION:  1 . . 5
         (C) IDENTIFICATION METHOD:   Synthesis; verified by FAB mass
             spectroscopy and amino acid analysis (ix) FEATURE:
         (A) NAME/KEY:  misc-feature
         (B) LOCATION:  1
         (C) IDENTIFICATION METHOD:   Synthesis
         (D) OTHER INFORMATION: Xaa is Val-tetramethylrhodamine

```
-continued (ix) FEATURE:
         (A) NAME/KEY:  misc-feature
         (B) LOCATION:  5
         (C) IDENTIFICATION METHOD:  Synthesis
         (D) OTHER INFORMATION: Xaa is Lys-tetramethylrhodamine (ix) FEATURE:
         (A) NAME/KEY:  cleavage site
         (B) LOCATION:  3 . . 4
         (C) IDENTIFICATION METHOD:  Synthesis; verified by FAB mass
             spectroscopy and amino acid analysis
         (D) OTHER INFORMATION: Enzyme Substrate (xi) SEQUENCE DESCRIPTION: SEQ ID NO: 2:

Xaa Pro Arg Gly Xaa
1               5
```